(12) United States Patent
Heilman et al.

(10) Patent No.: US 7,045,552 B2
(45) Date of Patent: May 16, 2006

(54) PHARMACEUTICAL COMPOSITION FOR IMPROVED ADMINISTRATION OF HIV GP41-DERIVED PEPTIDES, AND ITS USE IN THERAPY

(75) Inventors: David Heilman, Hillsborough, NC (US); Jie Di, Chapel Hill, NC (US); Brian Bray, Graham, NC (US)

(73) Assignee: Trimeris, Inc., Morrisville, NC (US)

( * ) Notice: Subject to any disclaimer, the term of this patent is extended or adjusted under 35 U.S.C. 154(b) by 250 days.

(21) Appl. No.: 10/663,589

(22) Filed: Sep. 16, 2003

(65) Prior Publication Data

US 2004/0063637 A1    Apr. 1, 2004

Related U.S. Application Data

(60) Provisional application No. 60/414,441, filed on Sep. 27, 2002.

(51) Int. Cl.
*A61K 47/30* (2006.01)
(52) U.S. Cl. ............... 514/772.3; 514/772.1; 514/773; 530/300; 530/324; 424/78.07; 424/185.1; 424/186.1; 424/188.1
(58) Field of Classification Search ............... 530/300, 530/324; 424/78.07, 185.1, 186.1, 188.1; 514/772.1, 772.3, 773
See application file for complete search history.

(56) References Cited

U.S. PATENT DOCUMENTS

| | | | |
|---|---|---|---|
| 5,462,863 A | 10/1995 | Hsieh et al. | |
| 5,464,933 A | 11/1995 | Bolognesi et al. | |
| 5,589,167 A * | 12/1996 | Cleland et al. | ............ 424/85.7 |
| 5,656,480 A | 8/1997 | Wild et al. | |
| 6,004,549 A | 12/1999 | Reichert et al. | |
| 6,143,314 A * | 11/2000 | Chandrashekar et al. | ... 424/426 |
| 6,348,568 B1 | 2/2002 | Barney et al. | |
| 6,573,078 B1 | 6/2003 | Wild et al. | |
| 2004/0076602 A1* | 4/2004 | Harris | ..................... 424/78.38 |

OTHER PUBLICATIONS

Coombes et al. "Biodegradable polymeric microparticles of drug delivery and vaccine formulation: the surface attachment of hydrophilic species using the concept of poly(ethylene glycol) anchoring segments", Biomaterials, vol. 18, Issue 17 (Sep. 199.*

Middaugh et al., "Protein Solubility", Chapter 4 in "Stability of Protein Pharmaceuticals", edited by Ahern and Manning. Plenum Press, 1992, pp. 109-113.

Middaugh et al., "Determination of the apparent thermodynamic activities of saturated protein solutions", 1979, pp. 367-370, vol. 254, No. 3. The Journal of Biological Chemistry.

* cited by examiner

*Primary Examiner*—Jeffrey Stucker
(74) *Attorney, Agent, or Firm*—M. Bud Nelson

(57) ABSTRACT

Provided is a pharmaceutical composition comprising a solution comprised of synthetic peptide in a final concentration of not less than 70 mg/ml in admixture with a polyol; wherein the synthetic peptide is an HIV fusion inhibitor, and wherein the polyol is in a final concentration of no less than 5 weight % and no more than 75 weight % of the pharmaceutical composition. Also provided is a synthetic peptide-containing pharmaceutical composition as a unit dose comprising an aqueous formulation comprised of synthetic peptide in a final concentration of not less than 70 mg/ml in admixture with a polyol; wherein the synthetic peptide is an HIV fusion inhibitor, and wherein the polyol is in a final concentration of no less than 5 weight % and no more than 75 weight % of the pharmaceutical composition. Further provided is a method of treating HIV infection by administering to an HIV-infected individual a pharmaceutical composition according to the present invention.

24 Claims, 1 Drawing Sheet

SEQUENCE LISTING

```
<160> NUMBER OF SEQ ID NOS: 95

<210> SEQ ID NO 1
<211> LENGTH: 60
<212> TYPE: PRT
<213> ORGANISM: Human immunodeficiency virus type 1

<400> SEQUENCE: 1

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile Leu Ala Val
        35                  40                  45

Glu Arg Tyr Leu Lys Asp Gln Gln Leu Leu Gly Ile
    50                  55                  60

<210> SEQ ID NO 2
<211> LENGTH: 64
<212> TYPE: PRT
<213> ORGANISM: Human immunodeficiency virus type 1
```

-continued

```
<400> SEQUENCE: 2

Trp Asn Ala Ser Trp Ser Asn Lys Ser Leu Glu Gln Ile Trp Asn Asn
1               5                   10                  15

Met Thr Trp Met Glu Trp Asp Arg Glu Ile Asn Asn Tyr Thr Ser Leu
            20                  25                  30

Ile His Ser Leu Ile Glu Glu Ser Gln Asn Gln Gln Glu Lys Asn Glu
        35                  40                  45

Gln Glu Leu Leu Glu Leu Asp Lys Trp Ala Ser Leu Trp Asn Trp Phe
    50                  55                  60

<210> SEQ ID NO 3
<211> LENGTH: 38
<212> TYPE: PRT
<213> ORGANISM: Artificial
<220> FEATURE:
<223> OTHER INFORMATION: synthesized

<400> SEQUENCE: 3

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 4
<211> LENGTH: 36
<212> TYPE: PRT
<213> ORGANISM: Artificial
<220> FEATURE:
<223> OTHER INFORMATION: synthesized

<400> SEQUENCE: 4

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 5
<211> LENGTH: 39
<212> TYPE: PRT
<213> ORGANISM: Artificial
<220> FEATURE:
<223> OTHER INFORMATION: synthesized

<400> SEQUENCE: 5

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 6
<211> LENGTH: 43
<212> TYPE: PRT
<213> ORGANISM: Artificial
<220> FEATURE:
<223> OTHER INFORMATION: synthesized
```

<400> SEQUENCE: 6

Gly Ser Thr Met Gly Ala Arg Ser Met Thr Leu Thr Val Gln Ala Arg
1               5                   10                  15

Gln Leu Leu Ser Gly Ile Val Gln Gln Gln Asn Asn Leu Leu Arg Ala
            20                  25                  30

Ile Glu Ala Gln Gln His Leu Leu Gln Leu Thr
        35                  40

<210> SEQ ID NO 7
<211> LENGTH: 54
<212> TYPE: PRT
<213> ORGANISM: Artificial
<220> FEATURE:
<223> OTHER INFORMATION: synthesized

<400> SEQUENCE: 7

Gly Ser Thr Met Gly Ala Arg Ser Met Thr Leu Thr Val Gln Ala Arg
1               5                   10                  15

Gln Leu Leu Ser Gly Ile Val Gln Gln Gln Asn Asn Leu Leu Arg Ala
            20                  25                  30

Ile Glu Ala Gln Gln His Leu Leu Gln Leu Thr Val Trp Gly Ile Lys
        35                  40                  45

Gln Leu Gln Ala Arg Ile
    50

<210> SEQ ID NO 8
<211> LENGTH: 36
<212> TYPE: PRT
<213> ORGANISM: Artificial
<220> FEATURE:
<223> OTHER INFORMATION: synthesized

<400> SEQUENCE: 8

Gly Ala Arg Ser Met Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
            20                  25                  30

Gln His Leu Leu
        35

<210> SEQ ID NO 9
<211> LENGTH: 38
<212> TYPE: PRT
<213> ORGANISM: Artificial
<220> FEATURE:
<223> OTHER INFORMATION: synthesized

<400> SEQUENCE: 9

Gly Ala Arg Ser Met Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
            20                  25                  30

Gln His Leu Leu Gln Leu
        35

<210> SEQ ID NO 10
<211> LENGTH: 40
<212> TYPE: PRT
<213> ORGANISM: Artificial
<220> FEATURE:
<223> OTHER INFORMATION: synthesized

```
<400> SEQUENCE: 10

Gly Ala Arg Ser Met Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
            20                  25                  30

Gln His Leu Leu Gln Leu Thr Val
        35                  40

<210> SEQ ID NO 11
<211> LENGTH: 50
<212> TYPE: PRT
<213> ORGANISM: Artificial
<220> FEATURE:
<223> OTHER INFORMATION: synthesized

<400> SEQUENCE: 11

Gly Ala Arg Ser Met Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
            20                  25                  30

Gln His Leu Leu Gln Leu Thr Val Trp Gly Ile Lys Gln Leu Gln Ala
        35                  40                  45

Arg Ile
    50

<210> SEQ ID NO 12
<211> LENGTH: 36
<212> TYPE: PRT
<213> ORGANISM: Artificial
<220> FEATURE:
<223> OTHER INFORMATION: synthesized

<400> SEQUENCE: 12

Ala Arg Ser Met Thr Leu Thr Val Gln Ala Arg Gln Leu Leu Ser Gly
1               5                   10                  15

Ile Val Gln Gln Gln Asn Asn Leu Leu Arg Ala Ile Glu Ala Gln Gln
            20                  25                  30

His Leu Leu Gln
        35

<210> SEQ ID NO 13
<211> LENGTH: 36
<212> TYPE: PRT
<213> ORGANISM: Artificial
<220> FEATURE:
<223> OTHER INFORMATION: synthesized

<400> SEQUENCE: 13

Arg Ser Met Thr Leu Thr Val Gln Ala Arg Gln Leu Leu Ser Gly Ile
1               5                   10                  15

Val Gln Gln Gln Asn Asn Leu Leu Arg Ala Ile Glu Ala Gln Gln His
            20                  25                  30

Leu Leu Gln Leu
        35

<210> SEQ ID NO 14
<211> LENGTH: 36
<212> TYPE: PRT
<213> ORGANISM: Artificial
<220> FEATURE:
<223> OTHER INFORMATION: synthesized
```

-continued

```
<400> SEQUENCE: 14

Ser Met Thr Leu Thr Val Gln Ala Arg Gln Leu Leu Ser Gly Ile Val
1               5                   10                  15

Gln Gln Gln Asn Asn Leu Leu Arg Ala Ile Glu Ala Gln Gln His Leu
            20                  25                  30

Leu Gln Leu Thr
            35

<210> SEQ ID NO 15
<211> LENGTH: 35
<212> TYPE: PRT
<213> ORGANISM: Artificial
<220> FEATURE:
<223> OTHER INFORMATION: synthesized

<400> SEQUENCE: 15

Met Thr Leu Thr Val Gln Ala Arg Gln Leu Leu Ser Gly Ile Val Gln
1               5                   10                  15

Gln Gln Asn Asn Leu Leu Arg Ala Ile Glu Ala Gln Gln His Leu Leu
            20                  25                  30

Gln Leu Thr
        35

<210> SEQ ID NO 16
<211> LENGTH: 36
<212> TYPE: PRT
<213> ORGANISM: Artificial
<220> FEATURE:
<223> OTHER INFORMATION: synthesized

<400> SEQUENCE: 16

Met Thr Leu Thr Val Gln Ala Arg Gln Leu Leu Ser Gly Ile Val Gln
1               5                   10                  15

Gln Gln Asn Asn Leu Leu Arg Ala Ile Glu Ala Gln Gln His Leu Leu
            20                  25                  30

Gln Leu Thr Val
        35

<210> SEQ ID NO 17
<211> LENGTH: 34
<212> TYPE: PRT
<213> ORGANISM: Artificial
<220> FEATURE:
<223> OTHER INFORMATION: synthesized

<400> SEQUENCE: 17

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr

<210> SEQ ID NO 18
<211> LENGTH: 35
<212> TYPE: PRT
<213> ORGANISM: Artificial
<220> FEATURE:
<223> OTHER INFORMATION: synthesized

<400> SEQUENCE: 18

Thr Leu Thr Val Gln Ala Arg Gln Leu Leu Ser Gly Ile Val Gln Gln
1               5                   10                  15
```

```
Gln Asn Asn Leu Leu Arg Ala Ile Glu Ala Gln Gln His Leu Leu Gln
            20                  25                  30

Leu Thr Val
        35

<210> SEQ ID NO 19
<211> LENGTH: 36
<212> TYPE: PRT
<213> ORGANISM: Artificial
<220> FEATURE:
<223> OTHER INFORMATION: synthesized

<400> SEQUENCE: 19

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp
        35

<210> SEQ ID NO 20
<211> LENGTH: 37
<212> TYPE: PRT
<213> ORGANISM: Artificial
<220> FEATURE:
<223> OTHER INFORMATION: synthesized

<400> SEQUENCE: 20

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly
        35

<210> SEQ ID NO 21
<211> LENGTH: 38
<212> TYPE: PRT
<213> ORGANISM: Artificial
<220> FEATURE:
<223> OTHER INFORMATION: synthesized

<400> SEQUENCE: 21

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile
        35

<210> SEQ ID NO 22
<211> LENGTH: 44
<212> TYPE: PRT
<213> ORGANISM: Artificial
<220> FEATURE:
<223> OTHER INFORMATION: synthesized

<400> SEQUENCE: 22

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30
```

Leu Thr Val Trp Gly Ile Lys Gln Leu Gln Ala Arg
          35                  40

<210> SEQ ID NO 23
<211> LENGTH: 36
<212> TYPE: PRT
<213> ORGANISM: Artificial
<220> FEATURE:
<223> OTHER INFORMATION: synthesized

<400> SEQUENCE: 23

Leu Thr Val Gln Ala Arg Gln Leu Leu Ser Gly Ile Val Gln Gln Gln
1               5                   10                  15

Asn Asn Leu Leu Arg Ala Ile Glu Ala Gln Gln His Leu Leu Gln Leu
            20                  25                  30

Thr Val Trp Gly
            35

<210> SEQ ID NO 24
<211> LENGTH: 42
<212> TYPE: PRT
<213> ORGANISM: Artificial
<220> FEATURE:
<223> OTHER INFORMATION: synthesized

<400> SEQUENCE: 24

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu
            35                  40

<210> SEQ ID NO 25
<211> LENGTH: 47
<212> TYPE: PRT
<213> ORGANISM: Artificial
<220> FEATURE:
<223> OTHER INFORMATION: synthesized

<400> SEQUENCE: 25

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr
            35                  40                  45

<210> SEQ ID NO 26
<211> LENGTH: 49
<212> TYPE: PRT
<213> ORGANISM: Artificial
<220> FEATURE:
<223> OTHER INFORMATION: synthesized

<400> SEQUENCE: 26

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
            35                  40                  45

Lys

<210> SEQ ID NO 27
<211> LENGTH: 51
<212> TYPE: PRT
<213> ORGANISM: Artificial
<220> FEATURE:
<223> OTHER INFORMATION: synthesized

<400> SEQUENCE: 27

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln
    50

<210> SEQ ID NO 28
<211> LENGTH: 36
<212> TYPE: PRT
<213> ORGANISM: Artificial
<220> FEATURE:
<223> OTHER INFORMATION: synthesized

<400> SEQUENCE: 28

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
        35

<210> SEQ ID NO 29
<211> LENGTH: 45
<212> TYPE: PRT
<213> ORGANISM: Artificial
<220> FEATURE:
<223> OTHER INFORMATION: synthesized

<400> SEQUENCE: 29

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu Ala Val Glu Arg Tyr Leu Lys Asp Gln
        35                  40                  45

<210> SEQ ID NO 30
<211> LENGTH: 41
<212> TYPE: PRT
<213> ORGANISM: Artificial
<220> FEATURE:
<223> OTHER INFORMATION: synthesized

<400> SEQUENCE: 30

Gln Gln Gln Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
            35                  40

<210> SEQ ID NO 31
<211> LENGTH: 34
<212> TYPE: PRT
<213> ORGANISM: Artificial
<220> FEATURE:
<223> OTHER INFORMATION: synthesized

<400> SEQUENCE: 31

Arg Ala Ile Glu Ala Gln Gln His Leu Leu Gln Leu Thr Val Trp Gly
1               5                   10                  15

Ile Lys Gln Leu Gln Ala Arg Ile Leu Ala Val Glu Arg Tyr Leu Lys
            20                  25                  30

Asp Gln

<210> SEQ ID NO 32
<211> LENGTH: 36
<212> TYPE: PRT
<213> ORGANISM: Artificial
<220> FEATURE:
<223> OTHER INFORMATION: synthesized

<400> SEQUENCE: 32

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu
            35

<210> SEQ ID NO 33
<211> LENGTH: 41
<212> TYPE: PRT
<213> ORGANISM: Artificial
<220> FEATURE:
<223> OTHER INFORMATION: synthesized

<400> SEQUENCE: 33

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
            35                  40

<210> SEQ ID NO 34
<211> LENGTH: 31
<212> TYPE: PRT
<213> ORGANISM: Artificial
<220> FEATURE:
<223> OTHER INFORMATION: synthesized

<400> SEQUENCE: 34

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val
            20                  25                  30

<210> SEQ ID NO 35
<211> LENGTH: 41
<212> TYPE: PRT

<213> ORGANISM: Artificial
<220> FEATURE:
<223> OTHER INFORMATION: synthesized

<400> SEQUENCE: 35

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln Gly Gly Cys
        35                  40

<210> SEQ ID NO 36
<211> LENGTH: 44
<212> TYPE: PRT
<213> ORGANISM: Artificial
<220> FEATURE:
<223> OTHER INFORMATION: synthesized

<400> SEQUENCE: 36

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln Gly Gly Cys
        35                  40

<210> SEQ ID NO 37
<211> LENGTH: 39
<212> TYPE: PRT
<213> ORGANISM: Artificial
<220> FEATURE:
<223> OTHER INFORMATION: synthesized

<400> SEQUENCE: 37

Leu Ser Gly Ile Val Gln Gln Gln Asn Asn Leu Leu Arg Ala Ile Glu
1               5                   10                  15

Ala Gln Gln His Leu Leu Gln Leu Thr Val Trp Gly Ile Lys Gln Leu
            20                  25                  30

Gln Ala Arg Ile Leu Ala Val
        35

<210> SEQ ID NO 38
<211> LENGTH: 36
<212> TYPE: PRT
<213> ORGANISM: Artificial
<220> FEATURE:
<223> OTHER INFORMATION: synthesized

<400> SEQUENCE: 38

Tyr Thr Asn Thr Ile Tyr Thr Leu Leu Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 39
<211> LENGTH: 36
<212> TYPE: PRT
<213> ORGANISM: Artificial
<220> FEATURE:
<223> OTHER INFORMATION: synthesized

```
<400> SEQUENCE: 39

Tyr Thr Gly Ile Ile Tyr Asn Leu Leu Glu Glu Ser Gln Asn Gln Gln
1               5                   10                  15

Glu Lys Asn Glu Gln Glu Leu Leu Glu Leu Asp Lys Trp Ala Asn Leu
            20                  25                  30

Trp Asn Trp Phe
        35

<210> SEQ ID NO 40
<211> LENGTH: 36
<212> TYPE: PRT
<213> ORGANISM: Artificial
<220> FEATURE:
<223> OTHER INFORMATION: synthesized

<400> SEQUENCE: 40

Tyr Thr Ser Leu Ile Tyr Ser Leu Leu Glu Lys Ser Gln Ile Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 41
<211> LENGTH: 36
<212> TYPE: PRT
<213> ORGANISM: Artificial
<220> FEATURE:
<223> OTHER INFORMATION: synthesized

<400> SEQUENCE: 41

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Phe Asn Phe Phe
        35

<210> SEQ ID NO 42
<211> LENGTH: 36
<212> TYPE: PRT
<213> ORGANISM: Artificial
<220> FEATURE:
<223> OTHER INFORMATION: synthesized

<400> SEQUENCE: 42

Trp Gln Glu Trp Glu Gln Lys Val Arg Tyr Leu Glu Ala Asn Ile Thr
1               5                   10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 43
<211> LENGTH: 42
<212> TYPE: PRT
<213> ORGANISM: Artificial
<220> FEATURE:
<223> OTHER INFORMATION: synthesized

<400> SEQUENCE: 43
```

```
Asp Arg Glu Ile Asn Asn Tyr Thr Ser Leu Ile His Ser Leu Ile Glu
1               5                   10                  15

Glu Ser Gln Asn Gln Gln Lys Asn Glu Gln Glu Leu Leu Glu Leu
            20                  25                  30

Asp Lys Trp Ala Ser Leu Trp Asn Trp Phe
        35                  40
```

<210> SEQ ID NO 44
<211> LENGTH: 48
<212> TYPE: PRT
<213> ORGANISM: Artificial
<220> FEATURE:
<223> OTHER INFORMATION: synthesized

<400> SEQUENCE: 44

```
Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45
```

<210> SEQ ID NO 45
<211> LENGTH: 42
<212> TYPE: PRT
<213> ORGANISM: Artificial
<220> FEATURE:
<223> OTHER INFORMATION: synthesized

<400> SEQUENCE: 45

```
Asn Asn Met Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys
        35                  40
```

<210> SEQ ID NO 46
<211> LENGTH: 46
<212> TYPE: PRT
<213> ORGANISM: Artificial
<220> FEATURE:
<223> OTHER INFORMATION: synthesized

<400> SEQUENCE: 46

```
Trp Gln Glu Trp Glu Gln Lys Val Arg Tyr Leu Glu Ala Asn Ile Thr
1               5                   10                  15

Ala Leu Leu Glu Gln Ala Gln Ile Gln Gln Glu Lys Asn Glu Tyr Glu
            20                  25                  30

Leu Gln Lys Leu Asp Lys Trp Ala Ser Leu Trp Asn Trp Phe
        35                  40                  45
```

<210> SEQ ID NO 47
<211> LENGTH: 50
<212> TYPE: PRT
<213> ORGANISM: Artificial
<220> FEATURE:
<223> OTHER INFORMATION: synthesized

<400> SEQUENCE: 47

```
Asn Asn Met Thr Trp Gln Glu Trp Glu Gln Lys Val Arg Tyr Leu Glu
1               5                   10                  15
```

```
Ala Asn Ile Thr Ala Leu Leu Glu Gln Ala Gln Ile Gln Gln Glu Lys
            20                  25                  30

Asn Glu Tyr Glu Leu Gln Lys Leu Asp Lys Trp Ala Ser Leu Trp Asn
        35                  40                  45

Trp Phe
    50
```

```
<210> SEQ ID NO 48
<211> LENGTH: 36
<212> TYPE: PRT
<213> ORGANISM: Artificial
<220> FEATURE:
<223> OTHER INFORMATION: synthesized

<400> SEQUENCE: 48

Trp Asn Trp Phe Ile Thr Ala Leu Leu Glu Gln Ala Gln Ile Gln Gln
1               5                   10                  15

Glu Lys Asn Glu Tyr Glu Leu Gln Lys Leu Asp Lys Trp Ala Ser Leu
            20                  25                  30

Trp Asn Trp Phe
        35
```

```
<210> SEQ ID NO 49
<211> LENGTH: 46
<212> TYPE: PRT
<213> ORGANISM: Artificial
<220> FEATURE:
<223> OTHER INFORMATION: synthesized

<400> SEQUENCE: 49

Trp Gln Glu Trp Asp Arg Glu Ile Ser Asn Tyr Thr Ser Leu Ile Thr
1               5                   10                  15

Ala Leu Leu Glu Gln Ala Gln Ile Gln Gln Glu Lys Asn Glu Tyr Glu
            20                  25                  30

Leu Gln Lys Leu Asp Glu Trp Ala Ser Leu Trp Glu Trp Phe
        35                  40                  45
```

```
<210> SEQ ID NO 50
<211> LENGTH: 40
<212> TYPE: PRT
<213> ORGANISM: Artificial
<220> FEATURE:
<223> OTHER INFORMATION: synthesized

<400> SEQUENCE: 50

Trp Gln Glu Trp Glu Arg Glu Ile Ser Ala Tyr Thr Ser Leu Ile Thr
1               5                   10                  15

Ala Leu Leu Glu Gln Ala Gln Ile Gln Gln Glu Lys Ile Glu Tyr Glu
            20                  25                  30

Leu Gln Lys Leu Glu Trp Glu Trp
        35                  40
```

```
<210> SEQ ID NO 51
<211> LENGTH: 39
<212> TYPE: PRT
<213> ORGANISM: Artificial
<220> FEATURE:
<223> OTHER INFORMATION: synthesized

<400> SEQUENCE: 51

Trp Gln Glu Trp Asp Arg Glu Ile Thr Ala Leu Leu Glu Gln Ala Gln
1               5                   10                  15
```

-continued

Ile Gln Gln Glu Lys Asn Glu Tyr Glu Leu Gln Lys Leu Asp Lys Trp
            20                  25                  30

Ala Ser Leu Trp Asn Trp Phe
        35

<210> SEQ ID NO 52
<211> LENGTH: 39
<212> TYPE: PRT
<213> ORGANISM: Artificial
<220> FEATURE:
<223> OTHER INFORMATION: synthesized

<400> SEQUENCE: 52

Trp Gln Glu Trp Asp Arg Glu Ile Thr Ala Leu Leu Glu Gln Ala Gln
1               5                   10                  15

Ile Gln Gln Glu Lys Asn Glu Tyr Glu Leu Gln Lys Leu Asp Glu Trp
            20                  25                  30

Ala Ser Leu Trp Glu Trp Phe
        35

<210> SEQ ID NO 53
<211> LENGTH: 35
<212> TYPE: PRT
<213> ORGANISM: Artificial
<220> FEATURE:
<223> OTHER INFORMATION: synthesized

<400> SEQUENCE: 53

Trp Gln Glu Trp Asp Arg Glu Ile Thr Ala Leu Leu Glu Gln Ala Gln
1               5                   10                  15

Ile Gln Gln Glu Lys Asn Glu Tyr Glu Leu Gln Lys Leu Asp Glu Trp
            20                  25                  30

Glu Trp Phe
        35

<210> SEQ ID NO 54
<211> LENGTH: 35
<212> TYPE: PRT
<213> ORGANISM: Artificial
<220> FEATURE:
<223> OTHER INFORMATION: synthesized

<400> SEQUENCE: 54

Trp Gln Glu Trp Glu Arg Glu Ile Thr Ala Leu Leu Glu Gln Ala Gln
1               5                   10                  15

Ile Gln Gln Glu Lys Ile Glu Tyr Glu Leu Gln Lys Leu Ile Glu Trp
            20                  25                  30

Glu Trp Phe
        35

<210> SEQ ID NO 55
<211> LENGTH: 35
<212> TYPE: PRT
<213> ORGANISM: Artificial
<220> FEATURE:
<223> OTHER INFORMATION: synthesized

<400> SEQUENCE: 55

Trp Gln Glu Trp Glu Arg Glu Ile Thr Ala Leu Leu Glu Gln Ala Gln
1               5                   10                  15

Ile Gln Gln Glu Lys Asn Glu Tyr Glu Leu Gln Lys Leu Ile Glu Trp
            20                  25                  30

Glu Trp Phe
        35

<210> SEQ ID NO 56
<211> LENGTH: 35
<212> TYPE: PRT
<213> ORGANISM: Artificial
<220> FEATURE:
<223> OTHER INFORMATION: synthesized

<400> SEQUENCE: 56

Trp Gln Glu Trp Glu Arg Glu Ile Thr Ala Leu Leu Glu Gln Ala Gln
1               5                   10                  15

Ile Gln Gln Glu Lys Ile Glu Tyr Glu Leu Gln Lys Leu Asp Glu Trp
            20                  25                  30

Glu Trp Phe
        35

<210> SEQ ID NO 57
<211> LENGTH: 39
<212> TYPE: PRT
<213> ORGANISM: Artificial
<220> FEATURE:
<223> OTHER INFORMATION: synthesized

<400> SEQUENCE: 57

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Asn Trp Phe
        35

<210> SEQ ID NO 58
<211> LENGTH: 39
<212> TYPE: PRT
<213> ORGANISM: Artificial
<220> FEATURE:
<223> OTHER INFORMATION: synthesized

<400> SEQUENCE: 58

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Gly Leu Trp Glu Trp Phe
        35

<210> SEQ ID NO 59
<211> LENGTH: 39
<212> TYPE: PRT
<213> ORGANISM: Artificial
<220> FEATURE:
<223> OTHER INFORMATION: synthesized

<400> SEQUENCE: 59

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Ala Glu Trp
            20                  25                  30

Ala Gly Leu Trp Ala Trp Phe
        35

```
<210> SEQ ID NO 60
<211> LENGTH: 35
<212> TYPE: PRT
<213> ORGANISM: Artificial
<220> FEATURE:
<223> OTHER INFORMATION: synthesized

<400> SEQUENCE: 60

Trp Gln Glu Trp Glu Gln Lys Ile Thr Ala Leu Leu Glu Gln Ala Gln
1               5                   10                  15

Ile Gln Gln Glu Lys Ile Glu Tyr Glu Leu Gln Lys Leu Ile Glu Trp
                20                  25                  30

Glu Trp Phe
            35

<210> SEQ ID NO 61
<211> LENGTH: 41
<212> TYPE: PRT
<213> ORGANISM: Artificial
<220> FEATURE:
<223> OTHER INFORMATION: synthesized

<400> SEQUENCE: 61

Gln Gln Gln Asn Asn Leu Leu Arg Ala Ile Glu Ala Gln Gln His Leu
1               5                   10                  15

Leu Gln Leu Thr Ala Trp Gly Ile Lys Gln Leu Gln Ala Arg Ile Leu
                20                  25                  30

Ala Val Glu Arg Tyr Leu Lys Asp Gln
            35                  40

<210> SEQ ID NO 62
<211> LENGTH: 41
<212> TYPE: PRT
<213> ORGANISM: Artificial
<220> FEATURE:
<223> OTHER INFORMATION: synthesized

<400> SEQUENCE: 62

Gln Gln Gln Asn Asn Leu Leu Arg Ala Ile Glu Ala Gln Gln His Leu
1               5                   10                  15

Leu Gln Leu Thr Val Ala Gly Ile Lys Gln Leu Gln Ala Arg Ile Leu
                20                  25                  30

Ala Val Glu Arg Tyr Leu Lys Asp Gln
            35                  40

<210> SEQ ID NO 63
<211> LENGTH: 49
<212> TYPE: PRT
<213> ORGANISM: Artificial
<220> FEATURE:
<223> OTHER INFORMATION: synthesized

<400> SEQUENCE: 63

Gln Ala Arg Gln Leu Leu Ser Gly Ile Val Gln Gln Gln Asn Asn Leu
1               5                   10                  15

Leu Arg Ala Ile Glu Ala Gln Gln His Ala Leu Gln Ala Thr Val Trp
                20                  25                  30

Gly Ile Lys Gln Leu Gln Ala Arg Ile Leu Ala Val Glu Arg Tyr Leu
            35                  40                  45

Lys
```

<210> SEQ ID NO 64
<211> LENGTH: 51
<212> TYPE: PRT
<213> ORGANISM: Artificial
<220> FEATURE:
<223> OTHER INFORMATION: synthesized

<400> SEQUENCE: 64

Gln Ala Arg Gln Leu Leu Ser Gly Ile Val Gln Gln Asn Asn Leu
1               5                   10                  15

Leu Arg Ala Ile Glu Ala Gln Gln His Ala Leu Gln Ala Thr Val Trp
            20                  25                  30

Gly Ile Lys Gln Leu Gln Ala Arg Ile Leu Ala Val Glu Arg Tyr Leu
        35                  40                  45

Lys Asp Gln
    50

<210> SEQ ID NO 65
<211> LENGTH: 49
<212> TYPE: PRT
<213> ORGANISM: Artificial
<220> FEATURE:
<223> OTHER INFORMATION: synthesized

<400> SEQUENCE: 65

Gln Ala Arg Gln Leu Val Ser Gly Leu Val Gln Gln Asn Asn Ile
1               5                   10                  15

Leu Arg Ala Leu Glu Ala Thr Gln His Ala Val Gln Ala Leu Val Trp
            20                  25                  30

Gly Val Lys Gln Leu Gln Ala Arg Val Leu Ala Leu Glu Arg Tyr Ile
        35                  40                  45

Lys

<210> SEQ ID NO 66
<211> LENGTH: 49
<212> TYPE: PRT
<213> ORGANISM: Artificial
<220> FEATURE:
<223> OTHER INFORMATION: synthesized

<400> SEQUENCE: 66

Gln Ile Arg Gln Leu Leu Ser Gly Ile Val Gln Gln Asn Asn Leu
1               5                   10                  15

Leu Arg Ala Ile Glu Ala Ile Gln His Ala Leu Gln Ala Ile Val Trp
            20                  25                  30

Gly Ile Lys Gln Leu Gln Ala Arg Ile Leu Ala Val Glu Arg Tyr Leu
        35                  40                  45

Lys

<210> SEQ ID NO 67
<211> LENGTH: 49
<212> TYPE: PRT
<213> ORGANISM: Artificial
<220> FEATURE:
<223> OTHER INFORMATION: synthesized

<400> SEQUENCE: 67

Gln Ala Arg Gln Leu Val Ser Gly Leu Val Gln Gln Asn Asn Ile
1               5                   10                  15

Leu Arg Ala Leu Glu Ala Thr Gln His Ala Val Gln Ala Leu Val Trp
            20                  25                  30

```
Gly Val Arg Gln Leu Gln Ala Arg Val Leu Ala Leu Glu Arg Tyr Ile
        35                  40                  45

Lys

<210> SEQ ID NO 68
<211> LENGTH: 51
<212> TYPE: PRT
<213> ORGANISM: Artificial
<220> FEATURE:
<223> OTHER INFORMATION: synthesized

<400> SEQUENCE: 68

Gln Ala Arg Gln Leu Leu Ser Gly Ile Val Gln Gln Gln Asn Asn Leu
1               5                  10                  15

Leu Arg Ala Ile Glu Ala Thr Gln His Ala Val Gln Ala Leu Val Trp
            20                  25                  30

Gly Val Lys Gln Leu Gln Ala Arg Val Leu Ala Leu Glu Arg Tyr Ile
        35                  40                  45

Lys Asp Gln
    50

<210> SEQ ID NO 69
<211> LENGTH: 51
<212> TYPE: PRT
<213> ORGANISM: Artificial
<220> FEATURE:
<223> OTHER INFORMATION: synthesized

<400> SEQUENCE: 69

Gln Ala Arg Gln Leu Val Ser Gly Leu Val Gln Gln Gln Asn Asn Ile
1               5                  10                  15

Leu Arg Ala Leu Glu Ala Gln Gln His Ala Leu Gln Ala Thr Val Trp
            20                  25                  30

Gly Ile Lys Gln Leu Gln Ala Arg Val Leu Ala Leu Glu Arg Tyr Ile
        35                  40                  45

Lys Asp Gln
    50

<210> SEQ ID NO 70
<211> LENGTH: 51
<212> TYPE: PRT
<213> ORGANISM: Artificial
<220> FEATURE:
<223> OTHER INFORMATION: synthesized

<400> SEQUENCE: 70

Gln Ala Arg Gln Leu Leu Ser Gly Ile Val Gln Gln Gln Asn Asn Leu
1               5                  10                  15

Leu Arg Ala Ile Glu Ala Gln Gln His Ala Leu Gln Ala Thr Val Trp
            20                  25                  30

Gly Val Lys Gln Leu Gln Ala Arg Ile Leu Ala Val Glu Arg Tyr Leu
        35                  40                  45

Lys Asp Gln
    50

<210> SEQ ID NO 71
<211> LENGTH: 41
<212> TYPE: PRT
<213> ORGANISM: Artificial
<220> FEATURE:
<223> OTHER INFORMATION: synthesized
```

-continued

<400> SEQUENCE: 71

Gln Gln Gln Asn Asn Leu Leu Arg Ala Ile Glu Ala Gln Gln His Leu
1               5                   10                  15

Leu Gln Leu Thr Val Phe Gly Ile Lys Gln Leu Gln Ala Arg Ile Leu
            20                  25                  30

Ala Val Glu Arg Tyr Leu Lys Asp Gln
        35                  40

<210> SEQ ID NO 72
<211> LENGTH: 49
<212> TYPE: PRT
<213> ORGANISM: Artificial
<220> FEATURE:
<223> OTHER INFORMATION: synthesized

<400> SEQUENCE: 72

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Phe
            20                  25                  30

Gly Ile Arg Gln Leu Gln Ala Arg Ile Leu Ala Val Glu Arg Tyr Leu
        35                  40                  45

Lys

<210> SEQ ID NO 73
<211> LENGTH: 51
<212> TYPE: PRT
<213> ORGANISM: Artificial
<220> FEATURE:
<223> OTHER INFORMATION: synthesized

<400> SEQUENCE: 73

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Ala Thr Val Trp
            20                  25                  30

Gly Ile Lys Gln Leu Gln Ala Arg Ile Leu Ala Val Glu Arg Tyr Leu
        35                  40                  45

Lys Asp Gln
    50

<210> SEQ ID NO 74
<211> LENGTH: 41
<212> TYPE: PRT
<213> ORGANISM: Artificial
<220> FEATURE:
<223> OTHER INFORMATION: synthesized

<400> SEQUENCE: 74

Gln Gln Gln Asn Asn Leu Leu Arg Ala Ile Glu Ala Gln Gln His Leu
1               5                   10                  15

Leu Gln Ala Thr Val Trp Gly Ile Lys Gln Leu Gln Ala Arg Ile Leu
            20                  25                  30

Ala Val Glu Arg Tyr Leu Lys Asp Gln
        35                  40

<210> SEQ ID NO 75
<211> LENGTH: 36
<212> TYPE: PRT
<213> ORGANISM: Artificial
<220> FEATURE:

<223> OTHER INFORMATION: synthesized

<400> SEQUENCE: 75

Asn Ala Ser Trp Ser Asn Lys Ser Leu Glu Gln Ile Trp Asn Asn Met
1               5                   10                  15

Thr Trp Met Glu Trp Asp Arg Glu Ile Asn Asn Tyr Thr Ser Leu Ile
            20                  25                  30

His Ser Leu Ile
        35

<210> SEQ ID NO 76
<211> LENGTH: 36
<212> TYPE: PRT
<213> ORGANISM: Artificial
<220> FEATURE:
<223> OTHER INFORMATION: synthesized

<400> SEQUENCE: 76

Asn Lys Ser Leu Glu Gln Ile Trp Asn Asn Met Thr Trp Met Glu Trp
1               5                   10                  15

Asp Arg Glu Ile Asn Asn Tyr Thr Ser Leu Ile His Ser Leu Ile Glu
            20                  25                  30

Glu Ser Gln Asn
        35

<210> SEQ ID NO 77
<211> LENGTH: 36
<212> TYPE: PRT
<213> ORGANISM: Artificial
<220> FEATURE:
<223> OTHER INFORMATION: synthesized

<400> SEQUENCE: 77

Lys Ser Leu Glu Gln Ile Trp Asn Asn Met Thr Trp Met Glu Trp Asp
1               5                   10                  15

Arg Glu Ile Asn Asn Tyr Thr Ser Leu Ile His Ser Leu Ile Glu Glu
            20                  25                  30

Ser Gln Asn Gln
        35

<210> SEQ ID NO 78
<211> LENGTH: 36
<212> TYPE: PRT
<213> ORGANISM: Artificial
<220> FEATURE:
<223> OTHER INFORMATION: synthesized

<400> SEQUENCE: 78

Ser Leu Glu Gln Ile Trp Asn Asn Met Thr Trp Met Glu Trp Asp Arg
1               5                   10                  15

Glu Ile Asn Asn Tyr Thr Ser Leu Ile His Ser Leu Ile Glu Glu Ser
            20                  25                  30

Gln Asn Gln Gln
        35

<210> SEQ ID NO 79
<211> LENGTH: 36
<212> TYPE: PRT
<213> ORGANISM: Artificial
<220> FEATURE:
<223> OTHER INFORMATION: synthesized

<400> SEQUENCE: 79

-continued

Leu Glu Gln Ile Trp Asn Asn Met Thr Trp Met Glu Trp Asp Arg Glu
1               5                   10                  15

Ile Asn Asn Tyr Thr Ser Leu Ile His Ser Leu Ile Glu Glu Ser Gln
                20                  25                  30

Asn Gln Gln Glu
        35

<210> SEQ ID NO 80
<211> LENGTH: 36
<212> TYPE: PRT
<213> ORGANISM: Artificial
<220> FEATURE:
<223> OTHER INFORMATION: synthesized

<400> SEQUENCE: 80

Glu Gln Ile Trp Asn Asn Met Thr Trp Met Glu Trp Asp Arg Glu Ile
1               5                   10                  15

Asn Asn Tyr Thr Ser Leu Ile His Ser Leu Ile Glu Glu Ser Gln Asn
                20                  25                  30

Gln Gln Glu Lys
        35

<210> SEQ ID NO 81
<211> LENGTH: 36
<212> TYPE: PRT
<213> ORGANISM: Artificial
<220> FEATURE:
<223> OTHER INFORMATION: synthesized

<400> SEQUENCE: 81

Gln Ile Trp Asn Asn Met Thr Trp Met Glu Trp Asp Arg Glu Ile Asn
1               5                   10                  15

Asn Tyr Thr Ser Leu Ile His Ser Leu Ile Glu Glu Ser Gln Asn Gln
                20                  25                  30

Gln Glu Lys Asn
        35

<210> SEQ ID NO 82
<211> LENGTH: 36
<212> TYPE: PRT
<213> ORGANISM: Artificial
<220> FEATURE:
<223> OTHER INFORMATION: synthesized

<400> SEQUENCE: 82

Ile Trp Asn Asn Met Thr Trp Met Glu Trp Asp Arg Glu Ile Asn Asn
1               5                   10                  15

Tyr Thr Ser Leu Ile His Ser Leu Ile Glu Glu Ser Gln Asn Gln Gln
                20                  25                  30

Glu Lys Asn Glu
        35

<210> SEQ ID NO 83
<211> LENGTH: 36
<212> TYPE: PRT
<213> ORGANISM: Artificial
<220> FEATURE:
<223> OTHER INFORMATION: synthesized

<400> SEQUENCE: 83

Trp Asn Asn Met Thr Trp Met Glu Trp Asp Arg Glu Ile Asn Asn Tyr
1               5                   10                  15

-continued

Thr Ser Leu Ile His Ser Leu Ile Glu Glu Ser Gln Asn Gln Gln Glu
            20                  25                  30

Lys Asn Glu Gln
        35

<210> SEQ ID NO 84
<211> LENGTH: 36
<212> TYPE: PRT
<213> ORGANISM: Artificial
<220> FEATURE:
<223> OTHER INFORMATION: synthesized

<400> SEQUENCE: 84

Asn Asn Met Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu
        35

<210> SEQ ID NO 85
<211> LENGTH: 36
<212> TYPE: PRT
<213> ORGANISM: Artificial
<220> FEATURE:
<223> OTHER INFORMATION: synthesized

<400> SEQUENCE: 85

Asn Met Thr Trp Met Glu Trp Asp Arg Glu Ile Asn Asn Tyr Thr Ser
1               5                   10                  15

Leu Ile His Ser Leu Ile Glu Glu Ser Gln Asn Gln Gln Glu Lys Asn
            20                  25                  30

Glu Gln Glu Leu
        35

<210> SEQ ID NO 86
<211> LENGTH: 36
<212> TYPE: PRT
<213> ORGANISM: Artificial
<220> FEATURE:
<223> OTHER INFORMATION: synthesized

<400> SEQUENCE: 86

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu
        35

<210> SEQ ID NO 87
<211> LENGTH: 36
<212> TYPE: PRT
<213> ORGANISM: Artificial
<220> FEATURE:
<223> OTHER INFORMATION: synthesized

<400> SEQUENCE: 87

Thr Trp Met Glu Trp Asp Arg Glu Ile Asn Asn Tyr Thr Ser Leu Ile
1               5                   10                  15

His Ser Leu Ile Glu Glu Ser Gln Asn Gln Gln Glu Lys Asn Glu Gln
            20                  25                  30

Glu Leu Leu Glu
        35

<210> SEQ ID NO 88
<211> LENGTH: 36
<212> TYPE: PRT
<213> ORGANISM: Artificial
<220> FEATURE:
<223> OTHER INFORMATION: synthesized

<400> SEQUENCE: 88

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 89
<211> LENGTH: 35
<212> TYPE: PRT
<213> ORGANISM: Artificial
<220> FEATURE:
<223> OTHER INFORMATION: synthesized

<400> SEQUENCE: 89

Met Glu Trp Asp Arg Glu Ile Asn Asn Tyr Thr Ser Leu Ile His Ser
1               5                   10                  15

Leu Ile Glu Glu Ser Gln Asn Gln Gln Glu Lys Asn Glu Gln Glu Leu
            20                  25                  30

Leu Glu Asp
        35

<210> SEQ ID NO 90
<211> LENGTH: 36
<212> TYPE: PRT
<213> ORGANISM: Artificial
<220> FEATURE:
<223> OTHER INFORMATION: synthesized

<400> SEQUENCE: 90

Glu Trp Asp Arg Glu Ile Asn Asn Tyr Thr Ser Leu Ile His Ser Leu
1               5                   10                  15

Ile Glu Glu Ser Gln Asn Gln Gln Glu Lys Asn Glu Gln Glu Leu Leu
            20                  25                  30

Glu Leu Asp Lys
        35

<210> SEQ ID NO 91
<211> LENGTH: 36
<212> TYPE: PRT
<213> ORGANISM: Artificial
<220> FEATURE:
<223> OTHER INFORMATION: synthesized

<400> SEQUENCE: 91

Trp Asp Arg Glu Ile Asn Asn Tyr Thr Ser Leu Ile His Ser Leu Ile
1               5                   10                  15

Glu Glu Ser Gln Asn Gln Gln Glu Lys Asn Glu Gln Glu Leu Leu Glu
            20                  25                  30

Leu Asp Lys Trp
        35

<210> SEQ ID NO 92
<211> LENGTH: 36
<212> TYPE: PRT
<213> ORGANISM: Artificial
<220> FEATURE:
<223> OTHER INFORMATION: synthesized

<400> SEQUENCE: 92

Asn Tyr Thr Ser Leu Ile His Ser Leu Ile Glu Glu Ser Gln Asn Gln
1               5                   10                  15

Gln Glu Lys Asn Glu Gln Glu Leu Leu Glu Leu Asp Lys Trp Ala Ser
            20                  25                  30

Leu Trp Asn Trp
        35

<210> SEQ ID NO 93
<211> LENGTH: 36
<212> TYPE: PRT
<213> ORGANISM: Artificial
<220> FEATURE:
<223> OTHER INFORMATION: synthesized

<400> SEQUENCE: 93

Thr Ser Leu Ile His Ser Leu Ile Glu Glu Ser Gln Asn Gln Gln Glu
1               5                   10                  15

Lys Asn Glu Gln Glu Leu Leu Glu Leu Asp Lys Trp Ala Ser Leu Trp
            20                  25                  30

Asn Trp Phe Asn
        35

<210> SEQ ID NO 94
<211> LENGTH: 36
<212> TYPE: PRT
<213> ORGANISM: Artificial
<220> FEATURE:
<223> OTHER INFORMATION: synthesized

<400> SEQUENCE: 94

Ser Leu Ile His Ser Leu Ile Glu Glu Ser Gln Asn Gln Gln Glu Lys
1               5                   10                  15

Asn Glu Gln Glu Leu Leu Glu Leu Asp Lys Trp Ala Ser Leu Trp Asn
            20                  25                  30

Trp Phe Asn Ile
        35

<210> SEQ ID NO 95
<211> LENGTH: 36
<212> TYPE: PRT
<213> ORGANISM: Artificial
<220> FEATURE:
<223> OTHER INFORMATION: synthesized

<400> SEQUENCE: 95

Leu Ile His Ser Leu Ile Glu Glu Ser Gln Asn Gln Gln Glu Lys Asn
1               5                   10                  15

Glu Gln Glu Leu Leu Glu Leu Asp Lys Trp Ala Ser Leu Trp Asn Trp
            20                  25                  30

Phe Asn Ile Thr
        35

PHARMACEUTICAL COMPOSITION FOR IMPROVED ADMINISTRATION OF HIV GP41-DERIVED PEPTIDES, AND ITS USE IN THERAPY

This application claims the benefit of the U.S. Provisional application No. 60/414,441 filed on Sep. 27, 2002.

FIELD OF THE INVENTION

The present invention relates to a pharmaceutical composition comprised of polymer admixed with synthetic peptides derived from Human Immunodeficiency Virus (HIV) gp41. More particularly, the present invention comprises a pharmaceutical composition comprising a mixture of a polyol with synthetic peptide having an amino acid sequence derived from either the HR1 region or the HR2 region of HIV gp41.

BACKGROUND OF THE INVENTION

It is now well known that cells can be infected by HIV through a process by which fusion occurs between the cellular membrane and the viral membrane. The generally accepted model of this process is that the viral envelope glycoprotein complex (gp120/gp41) interact with cell surface receptors on the membranes of the target cells. Following binding of gp120 to cellular receptors (e.g., CD4 in combination with a chemokine co-receptor such as CCR-5 or CXCR-4), induced is a conformational change in the gp120/gp41 complex that allows gp41 to insert into the membrane of the target cell and mediate membrane fusion.

The amino acid sequence of gp41, and its variation among different strains of HIV, is well known. FIG. 1 is a schematic representation of the generally accepted functional domains of gp41 (note the amino acid sequence numbers may vary slightly depending on the HIV strain). The fusion peptide (fusogenic domain) is believed to be involved in insertion into and disruption of the target cell membrane. The transmembrane domain, containing the transmembrane anchor sequence, is located at the C-terminal end of the protein. Between the fusion peptide and transmembrane anchor are two distinct regions, known as heptad repeat (HR) regions, each region having a plurality of heptads. One region, HR1, nearer to the N-terminal end of the protein, has been generally described as comprising amino acid residues from about 545 to about 595 of the amino acid sequence of gp160 (SEQ ID NO:1). However, the amino acid numbering of gp160 depends on the strain from which the amino acid sequence was deduced. The amino acid sequence comprising the HR1 region and the amino acid sequence comprising the HR2 region are each highly conserved regions in the HIV-1 envelope protein (Shu et al., 1999, *Biochemistry,* 38:5378–5385; Hanna et al., 2002, *AIDS* 16:1603–8). The HR2 region, nearer to the C-terminal end of the protein as compared to the HR1 region, has been generally described as comprising amino acids in the positions from about 628 to about 678 of the amino acid sequence of gp160 (SEQ ID NO:2). The HR regions share structural and functional features. For example, each HR region has a plurality of 7 amino acid residue stretches or "heptads" (the 7 amino acids in each heptad designated "a" through "g"), wherein the amino acids in the "a" position and "d" position are generally hydrophobic. Also present in each HR region is one or more leucine zipper-like motifs (also referred to as "leucine zipper-like repeats") comprising an 8 amino acid sequence initiating with and ending with an isoleucine or leucine. Most frequently, the HR2 region has just one leucine zipper like-motif, whereas the HR1 region has five leucine zipper-like motifs. The heptads and leucine zipper-like motifs each contribute to formation of a coiled coil structure of gp41 and of a coiled coil structure of peptides derived from the HR regions. Generally, coiled coils are known to be comprised of two or more helices that wrap around each other in forming oligomers, with the hallmark of coiled coils being a heptad repeat of amino acids with a predominance of hydrophobic residues at the first ("a") and fourth ("d") positions, charged residues frequently at the fifth ("e") and seventh ("g") positions, and with the amino acids in the "a" position and "d" position being determinants that influence the oligomeric state and strand orientation (see, e.g., Akey et al., 2001, *Biochemistry,* 40:6352–60).

It was discovered that synthetic peptides derived from either the HR1 region ("HR1 peptides") or HR2 region ("HR2 peptides") of HIV gp41 inhibit transmission of HIV to host cells both in in vitro assays and in in vivo clinical studies (see, e.g., Wild et al., 1994, *Proc. Natl. Acad. Sci. USA,* 91:9770–9774; U.S. Pat. Nos. 5,464,933 and 5,656,480 licensed to the present assignee; and Kilby et al., 1998, *Nature Med.* 4:1302–1306). More particularly, HR1 peptides as exemplified by DP107 (also known as T21; SEQ ID NO:3) blocked infection of T cells with 50% effective concentration values (EC50) of 1 μg/ml (see, e.g., Lawless et al., 1996, *Biochemistry,* 35:13697–13708). HR2 peptides, as exemplified by DP178 (also known as T20; SEQ ID NO:4) blocked infection of T cells with 50% effective concentration values (EC50) in the ng/ml range. Pioneering potent synthetic peptides, which comprise one or more enhancer sequences linked to a core HIV gp41 amino acid sequence, inhibit HIV membrane fusion and thereby prevent transmission of the virus to a host cell, have been described previously (see, e.g., U.S. Pat. Nos. 6,258,782 and 6,348,568 assigned to the present assignee). Currently, like other peptides known in the art, to most efficiently deliver an amount effective for antiviral activity, such synthetic peptides are administered frequently (e.g., daily injections) to attain and maintain a level in the bloodstream sufficient for such a therapeutic effect. Additionally, injection site reactions are the most common adverse event in individuals receiving the currently available injectable solution formulations of HIV fusion inhibitors. For example, in one Phase III study of T20 administered subcutaneously, and using a mannitol-based formulation (without a polyol as taught in the present invention), injection site reactions (manifested by one or more of reddening, swelling, and discomfort at the injection site) were experienced by 98% of patients receiving treatment, with 3.3% of patients citing such reactions as a reason for discontinuing treatment. Another limitation with the current injectable solution formulation of HIV fusion inhibitors is that it is difficult to achieve a desirable injectable solution containing a concentration of synthetic peptide of no less than 100 mg/ml without problems of viscosity (where the formulation resembles a gel rather than a solution) and/or instability (e.g., precipitation, over a predetermined time period, of synthetic peptide out of solution).

Polyols, particularly polyethylene glycol (PEG), have been found to be well tolerated and are believed to have a relatively low level of toxicity when used as a pharmaceutically acceptable carrier in an injectable solution of a drug formulation. Thus, PEG has been used as a pharmaceutically acceptable carrier in a number of regulatory-approved injectable solution formulations that contain drug comprising chemical compositions other than peptides and proteins. The amount of PEG in such a formulation is typically present in an amount from about 0.1 weight percent to about 5 weight percent of the formulation. PEG has not been used as a pharmaceutically acceptable carrier for maintaining proteins and peptides in solution, but rather has been used in the precipitation of proteins and peptides. For example, hepatitis B surface antigen protein may be purified using a cycle of precipitation with from 1% to 10% PEG (w/v; see, e.g., U.S. Pat. No. 5,462,863); secretory IgA can be precipitated with PEG at a concentration of 15 to 25 weight per volume (w/v) percent of PEG; fibrinogen can be precipitated with PEG amounting to 2.5% by weight; asparaginase can be precipitated with a solution of 40 to 60 weight percent PEG, and antihemophilic factor may be precipitated at a final concentration of 3 percent to 6 percent PEG (w/v). Thus, one concern in using PEG at concentrations equal to or greater than 5 weight percent in a pharmaceutical composition as a pharmaceutically acceptable carrier is precipitation out of solution of the protein or peptide that is to be administered in an injectable solution formulation, a very undesirable effect. In one instance (see, e.g., U.S. Pat. No. 6,004,549), disclosed is a pharmaceutical composition comprised of a suspension of a protein in a polyol; i.e., a crystalline form of interferon suspended in a solution or gel containing 40% aqueous solution of PEG8000 (w/v) or a 50% solution of PEG 3350 (the number following "PEG" is approximate molecular size in daltons of the PEG referenced, as will be discussed in more detail herein).

However, a pharmaceutical composition comprised of a solution comprised of mixture of synthetic peptide (HIV fusion inhibitor) and a polyol such as PEG in a final concentration of no less than 5 weight percent (%) (e.g., weight/volume percent) and no more than 75 weight %, has not heretofor been disclosed. Until the discovery of the present invention there remained a long-felt need in the art for a formulation of a pharmaceutical composition which can (a) be used as an injectable solution, (b) contain synthetic peptide (HIV fusion inhibitor) in a concentration of no less than 100 mg/ml in a solution having sufficient stability for use for its intended purpose, and additionally, in possibly reducing the number of injections needed to administer an effective amount of synthetic peptide for achieving a therapeutic effect, and (c) which may minimize an injection site reaction. The present invention addresses these needs.

SUMMARY OF THE INVENTION

The present invention fills this need by providing a pharmaceutical composition comprised of a solution comprising synthetic peptide (HIV fusion inhibitor) in admixture with a polyol, wherein the polyol is in a final concentration of no less than 5 weight % and no more than 75 weight %, and more preferably no less than 10 weight % and no more than 50 weight %, of the pharmaceutical composition. The pharmaceutical composition comprises an injectable solution formulation that has unexpected results, and is a significant improvement, compared to currently used formulations. In particular, the pharmaceutical composition of the present invention comprises an injectable solution formulation which, when compared to the mannitol-based formulation or other formulation known in the art, (a) significantly reduces reconstitution time in preparing the pharmaceutical composition; (b) significantly reduces the viscosity of the pharmaceutical composition; (c) provides a suitable microenvironment surrounding synthetic peptide (HIV fusion inhibitor) which, among other benefits, allows a higher concentration (e.g., equal to or greater than 100 mg/ml) of synthetic peptide (HIV fusion inhibitor) to be put into solution and remain as a stable solution for a desired product life; and (d) may markedly reduce, in both incidence and intensity, injection site reactions when used as an injectable solution formulation.

The present invention further provides for a method of preparing a pharmaceutical composition according to the present invention comprising admixing a synthetic peptide with a polyol, wherein the polyol is in a final concentration of no less than 5 weight % and no more than 75 weight %, and more preferably no less than 10 weight % and no more than 50 weight %, of the pharmaceutical composition.

The present invention also provides for a method of treating HIV infection (preferably, HIV-1 infection) comprising administering to an HIV-infected individual a pharmaceutical composition according to the present invention. Preferably, the pharmaceutical composition is in an amount effective to inhibit transmission of HIV to a target cell, and/or in an amount effective to inhibit gp41-mediated fusion of HIV to a target cell.

Also provided is, in a synthetic peptide (HIV fusion inhibitor)-containing pharmaceutical composition as a unit dose, wherein the pharmaceutical composition comprises an aqueous formulation comprising: (a) a polyol present as a pharmaceutically acceptable carrier in an amount not less than 5 weight % and not more than 75 weight % of the pharmaceutical composition as a unit dose, and more preferably a polyol present as a pharmaceutically acceptable carrier in an amount not less than 10 weight % but not more than 50 weight % of the pharmaceutical composition as a unit dose; and (b) the synthetic peptide in an amount not less than 70 mg/ml and not more than 500 mg/ml, and more preferably, in an amount not less than 100 mg/ml and not more than 250 mg/ml. The present invention also provides for a method of treating HIV infection (preferably, HIV-1 infection) comprising administering to an HIV-infected individual a synthetic peptide (HIV fusion inhibitor)-containing pharmaceutical composition as a unit dose according to the present invention. Preferably, such pharmaceutical composition is in an amount effective to inhibit transmission of HIV to a target cell, and/or in an amount effective to inhibit gp41-mediated fusion of HIV to a target cell.

The above and other objects, features, and advantages of the present invention will be apparent in the following Detailed Description of the Invention when read in conjunction with accompanying drawings.

DETAILED DESCRIPTION OF THE INVENTION

Figure 1:
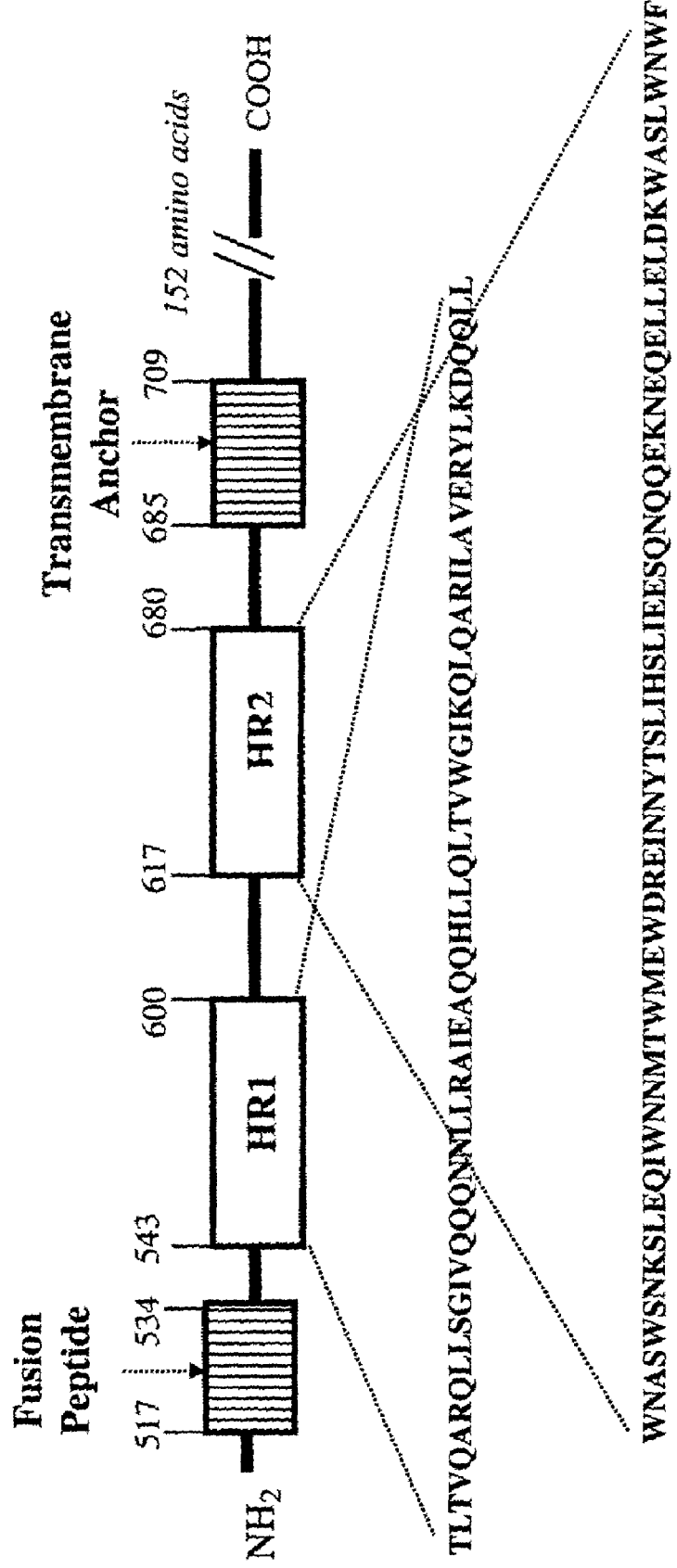
FIG. 1 is a schematic of HIV gp41 showing the heptad repeat 1 region (HR1) and heptad repeat 2 region (HR2) along with other functional regions of gp41. Exemplary peptide sequences corresponding to HIV-1 strain IIIB HR1 (SEQ ID NO:1) and HR2 (SEQ ID NO:2) are shown for purposes of illustration. The amino acid residues are numbered according to their position in gp160, strain $HIV_{IIIB}$.

Definitions:

The term "individual", when used herein for purposes of the specification and claims, means a mammal, and preferably a human.

The term "target cell", when used herein for purposes of the specification and claims, means a cell capable of being infected by HIV. Preferably, the cell is a human cell or are human cells; and more preferably, human cells capable of being infected by HIV via a process including membrane fusion.

The term "pharmaceutically acceptable carrier", when used herein for purposes of the specification and claims, means a carrier medium that does not significantly alter the biological activity of the active ingredient (e.g., a synthetic peptide comprising an HIV-fusion inhibitor) to which it is added. In accordance with the present invention, a polyol is a pharmaceutically acceptable carrier in the pharmaceutical composition comprising an injectable aqueous formulation according to the present invention. The pharmaceutical composition may comprise one or more additional pharmaceutically acceptable carriers other than polyol contained therein (i.e., one or more pharmaceutically acceptable carriers in addition to the polyol). As known to those skilled in the art, and for use in an injectable solution or aqueous formulation, a suitable pharmaceutically acceptable carrier may comprise one or more substances, including but not limited to, water, buffered water, saline, 0.3% glycine, aqueous alcohols, isotonic aqueous buffer; and may further include one or more substances such as glycerol, oils, salts such as sodium, potassium, magnesium and ammonium, phosphonates, carbonate esters, fatty acids, saccharides (e.g., mannitol), polysaccharides, excipients, and preservatives and/or stabilizers (to increase shelf-life or as necessary and suitable for manufacture and distribution of the composition). Preferably, the carrier is suitable for intravenous, intramuscular, subcutaneous or parenteral administration (e.g., by injection).

By the term "amino acid" is meant, for purposes of the specification and claims and in reference to the synthetic peptides used in the present invention, to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid (e.g., L-amino acid), a non-naturally occurring amino acid (e.g., D-amino acid), a synthetic amino acid, a modified amino acid, an amino acid derivative, an amino acid precursor, and a conservative substitution. One skilled in the art would know that the choice of amino acids incorporated into a peptide will depend, in part, on the specific physical, chemical or biological characteristics required of the antiviral peptide. Such characteristics are determined, in part, by determination of structure and function (e.g., antiviral activity; as described herein in more detail). For example, the skilled artisan would know from the descriptions herein that amino acids in a synthetic peptide may be comprised of one or more of naturally occurring (L)-amino acid and non-naturally occurring (D)-amino acid. A preferred amino acid may be used to the exclusion of amino acids other than the preferred amino acid.

A "conservative substitution", in relation to amino acid sequence of a synthetic peptide used in the present invention, is a term used hereinafter for the purposes of the specification and claims to mean one or more amino acids substitution in the sequence of the synthetic peptide such that the antiviral activity is substantially unchanged (e.g., if it inhibits HIV gp41-mediated fusion at a concentration in the nanomolar range before the substitution, after the substitution inhibition of HIV gp41-mediated fusion is observed in the nanomolar range). As known in the art "conservative substitution" is defined by aforementioned function, and includes substitutions of amino acids having substantially the same charge, size, hydrophilicity, and/or aromaticity as the amino acid replaced. Such substitutions are known to those of ordinary skill in the art to include, but are not limited to, glycine-alanine-valine; isoleucine-leucine; tryptophan-tyrosine; aspartic acid-glutamic acid; arginine-lysine; asparagine-glutamine; and serine-threonine. Such substitutions may also comprise polymorphisms at the various amino acid positions along the relevant HR region of gp41 found in laboratory and/or clinical isolates of HIV, which are readily available from public databases and are well known in the art.

The term "native sequence", when used herein for purposes of the specification and claims and in reference to the amino acid sequence of the HR1 region or of the HR2 region of HIV-1 gp41, means a naturally occurring sequence found in laboratory HIV strains and/or HIV clinical isolates. Such sequences are readily available from public gene databases such as GenBank, as are substitutions (e.g., polymorphisms) found in various amino acid positions of the amino acid sequence of the HR1 region and HR2 region of HIV gp41.

The term "polyol", when used herein for purposes of the specification and claims, means a polymer which is employed as a pharmaceutically acceptable carrier, and is preferably a water-soluble, polyalcohol which may include, but is not limited to, polyethylene glycol ("PEG"), polypropylene glycol ("PPG"), diethylene glycol, triethylene glycol, ethylene glycol, dipropylene glycol, copolymers comprising PPG (e.g., ethylene glycol/PPG), copolymers comprising PEG (e.g., PEG/PPG), and the like. A polyol encompasses both homopolymers and copolymers, and further may have a structure comprising a branched structure or linear structure as known to those skilled in the art. Preferably, the polymer is substantially non-toxic when used for in vivo applications in individuals. In a preferred embodiment, the polymer has a molecular weight in the range between about 200 daltons to about 20,000 daltons; and in a more preferred embodiment, the polymer has a molecular weight range between about 300 daltons to about 10,000 daltons. A preferred polymer for application in the present invention comprises a polyethylene glycol, and a more preferred polymer for application in the present invention comprises a polyethylene glycol having a molecular weight range, wherein the molecular weight range is no less than about 1,000 daltons and is no more than about 10,000 daltons. For example, a polyethylene glycol is comprised of a number of repeating oxyethylene groups, the average number of repeating oxyethylene groups generally correlating with the average molecular weight of the polyethylene glycol. In continuing this example, polyethylene glycol 6000 (PEG6000) has been described as having a molecular weight range of 5000 daltons to 7000 daltons (e.g., a molecular weight range which is no less than about 1,000 daltons and is no more than about 10,000 daltons). Similarly, PEG1500 has been described as having a molecular weight range of about 1430 daltons to about 1570 daltons. A preferred polymer may be applied to the present invention to the exclusion of a polymer other than the preferred polymer.

The terms "synthetic peptide" and "HIV fusion inhibitor" are used synonymously herein, in relation to a peptide employed in the present invention, and for the purposes of The terms "synthetic peptide" and "HIV fusion inhibitor" are used synonymously herein, in relation to a peptide employed in the present invention, and for the purposes of the specification and claims, to mean a peptide (a) produced by chemical synthesis, recombinant expression, biochemical or enzymatic fragmentation of a larger molecule, chemical cleavage of larger molecule, a combination of the foregoing or, in general, made by any other method in the art, and isolated; (b) comprising an amino acid sequence of no less than about 15 amino acids and no more than about 60 amino acid residues in length, and comprises of at least 10 contiguous amino acids contained in either the HR1 region or HR2 region of gp41 of HIV (more preferably of HIV-1); and (c) capable of inhibiting transmission of HIV to a target cell (preferably, by complexing to an HR region of HIV-1 gp41 and inhibiting fusion between HIV-1 and a target cell), as can be determined by assessing antiviral activity in vitro and/or in vivo, as will be described in more detail herein. The term "isolated" when used in reference to a peptide, means that the synthetic peptide is substantially free of components which have not become part of the integral structure of the peptide itself; e.g., such as substantially free of cellular material or culture medium when produced by recombinant techniques, or substantially free of chemical precursors or other chemicals when chemically synthesized or produced using biochemical or chemical processes. The synthetic peptide may comprise, in it's amino acid sequence, one or more conservative substitutions and/or one or polymorphisms found in the sequence of the relevant region of the HIV gp41 , or may comprise one or more amino acid substitutions which are added to stabilize helix structure and/or affect oligomerization so that the peptide self-assembles into a trimer (see, for example, the disclosure of co-pending U.S. application number 10/664,021 which is herein incorporated by reference); provided that it retains antiviral activity against HIV-1. Further, the amino acid sequence, in addition to having a core peptide derived from HIV gp41, may comprise one or more enhancer peptides linked to the core peptide, e.g., at the N-terminus, at the C-terminus or at both the N-terminus and C-terminus, or may have a core peptide derived from one or more of HIV-1, HIV-2, and SIV (see, e.g., U.S. Pat. No. 6,258,782, the disclosure of which is herein incorporated by reference). Depending on the synthetic peptide employed in the pharmaceutical composition, the synthetic peptide may exist as a monomer, or an oligomeric form which may include, but is not limited to, a dimer, trimer, tetramer, or hexamer. For example, synthetic peptides comprising modified HR1 peptides preferably self-assemble into trimers (e.g., a trimer being comprised of three molecules of synthetic peptide). Preferably, the synthetic peptide employed in the present invention may comprise a sequence of no less than about 15 amino acids and no more than about 60 amino acid residues in length, and preferably no less than 36 amino acids and no more than about 51 amino acids in length, and more preferably no less than about 41 amino acids and no more than about 51 amino acids in length. Preferably, for a synthetic peptide comprising sequence derived from the HR1 region of HIV-1 gp41, the synthetic peptide comprises a contiguous sequence of at least 15 amino acid residues in the amino acid sequence of SEQ ID NO:1, as key determinants in this portion of the HR1 region (e.g., such as, noted by single letter amino acid designation, NNLLRAIEAQQHLL QLTVWGIKQLQARI LAVERYLKD which is amino acid residue 18 to amino acid residue 54 of SEQ ID NO:1) have been found to influence structure, and biochemical and antiviral parameters described herein. Preferably, for a synthetic peptide sequence derived from the HR2 region of HIV gp41, the synthetic peptide comprises a contiguous sequence of at least 15 amino acid residues in the amino acid sequence of SEQ ID NO:2, and more preferably QQEKNEQEL (which is amino acid residue 43 to amino acid residue 51 of SEQ ID NO:2) as key determinants in this portion of the HR2 region have been found to influence structure, and biochemical and antiviral parameters described herein. Numerous of such synthetic peptides that may be applied to the present invention have been disclosed previously in, for example, U.S. Pat. Nos. 5,656,480, 6,133,418, and 6,258,782, (the disclosures of which are herein incorporated by reference in their entirety). For purposes of illustration, exemplary synthetic peptides that may be applied to the present invention include, but are not limited to, synthetic peptides comprising the amino acid sequence listed in SEQ ID NOs: 3–95. "Synthetic pepticle" when used herein with "polyol" or "PEG", with respect to being constituents (e.g., each as dissolved solids) in the pharmaceutical composition according to the present invention and for the purposes of the specification and claims, means that the synthetic peptide and polymer are not conjugated together (e.g., are not covalently bonded together).

The term "weight percent", as standard in the art and may be used synonymously with weight/volume percent, is used herein for the purposes of the specification and claims to mean milligrams (mg) of an ingredient in the pharmaceutical composition (e.g., polyol) per milliliter(s) (ml) of solution, multiplied by 0.1, as will be more apparent from the following descriptions herein.

The term "solution", as standard in the art in referring to an aqueous fluid into which is dissolved one or more solids, is used herein for the purposes of the specification and claims to mean an aqueous solution containing the synthetic peptide and polyol dissolved therein under realistic use conditions of concentration and temperature as described herein in more detail and as standard in the art for an injectable drug formulation. There are various ways known in the art to distinguish formation of a solution, as opposed to formation of a suspension, such as checking for visual clarity (transparency of a solution versus cloudiness of a suspension), light transmission, and the like.

The present invention is illustrated in the following examples, which are not intended to be limiting.

EXAMPLE 1

In this example, illustrated is a pharmaceutical composition according to the present invention, wherein several embodiments illustrated in this example employ T1249 (SEQ ID NO:5, see U.S. Pat. No. 6,258,752). However, it is understood (and shown by example herein) that synthetic peptide other than T1249 (SEQ ID NO:5) may be employed in the pharmaceutical composition according to the present invention, particularly because this class of synthetic peptides (HIV fusion inhibitor peptides) shares structural, biochemical, and functional features. More particularly, this class of synthetic peptides all comprise coiled coil heptad repeats which may contribute to the molecular interactions of solubility in an aqueous solution containing polyol as described herein in more detail. Other shared structural, biochemical and functional features include, but may not be limited to, an amino acid sequence containing one or more leucine zipper-like motifs, a propensity for coiled coil structure, a propensity for oligomerization, and ability to inhibit transmission of HIV to a target cell.

For use in the examples herein, peptides were synthesized on a peptide synthesizer using standard solid-phase synthesis techniques and using standard FMOC peptide chemistry or by peptide fragmentation and assembly as described in U.S. Pat. No. 6,281,331 (assigned to the present assignee, the disclosure of which is herein incorporated by reference).

In these examples, the synthetic peptides further comprised reactive functionalities; i.e., were blocked at the N-terminus by an acetyl group and at the C-terminus by an amide group. After cleavage from the resin, the synthetic peptides were precipitated, and the precipitate as lyophilized. The peptides were then purified using reverse-phase high performance liquid chromatography; and peptide identity was confirmed with electrospray mass spectrometry.

As illustrated in this example, provided is a pharmaceutical composition comprised of a solution comprising synthetic peptide in a final concentration of the pharmaceutical composition of not less than 100 mg/ml, and a polyol in a final concentration of no less than 5 weight % and no more than 75 weight %, and more preferably in a final concentration of no less than 10 weight % and no more than 50 weight %, of the pharmaceutical composition. Also provided is a synthetic peptide (HIV fusion inhibitor)-containing pharmaceutical composition as a unit dose, wherein the pharmaceutical composition comprises an aqueous formulation comprising: a polyol present as a pharmaceutically acceptable carrier in an amount not less than 5 weight % of the pharmaceutical composition as a unit dose, and more preferably, not less than 10 weight % of the pharmaceutical composition as a unit dose. In a preferred embodiment, the polyol is not more than 75 weight % of the pharmaceutical composition, and more preferably not more than 50 weight % of the pharmaceutical composition. Preferably, the synthetic peptide is in a final concentration of the pharmaceutical composition of not less than 70 mg/ml and not more than 500 mg/ml; and more preferably, of not less than 100 mg/ml and not more than 250 mg/ml. Further provided is a synthetic peptide (HIV fusion inhibitor peptide)-containing pharmaceutical composition as a unit dose, wherein the pharmaceutical composition comprises an aqueous formulation comprising a polyol as a pharmaceutically acceptable carrier in an amount not less than 10 weight % but not more than 50 weight % of the pharmaceutical composition as a unit dose. Preferably, the synthetic peptide is in a final concentration of the pharmaceutical composition of not less than 70 mg/ml and not more than 500 mg/ml; more preferably, of not less than 100 mg/ml and not more than 250 mg/ml.

Previous injectable solution formulations used clinically comprised T1249 (SEQ ID NO:5) in either a 12.5 mg/ml unit dosage, 25 mg/ml unit dosage, or 48 mg/ml unit dosage, based in formulation referred to as a "mannitol formulation". For example, the 48 mg/ml unit dosage comprised a lyophilized composition containing 55 mg of T1249, and 40 mg of mannitol which had been previously pH adjusted, and which is then reconstituted with 1.1 ml sterile water before injecting as a unit dosage. There was a long felt need for injectable solution formulations containing higher dosages (most desirably, not less than about 100 mg/ml per unit dose) of T1249 (SEQ ID NO:5). Various pharmaceutical compositions were formulated, as described in more detail herein, to address this need. Table 1 shows a comparison between a solution formulation containing a standard amount of PEG (e.g., about 0.5 weight percent) and synthetic peptide ("Formulation A") to a pharmaceutical composition of the present invention (e.g., no less than 10 weight %) ("Formulation B"), each reconstituted with 1.1 ml sterile water. Surprisingly, the pharmaceutical composition containing 10 weight % of PEG (Formulation B) significantly reduced the reconstitution time, as compared to Formulation A, yet still provided a solution which could be applied through a syringe ("syringibility" means passage through a 27 gauge needle consistent with that of an injectable solution used as a drug formulation). Content is as measured by high pressure liquid chromatography using methods standard in the art.

TABLE 1

|  | Formulation A | Formulation B |
|---|---|---|
| T-1249 (SEQ ID NO:5) | 118 mg/ml | 118 mg/ml |
| PEG 1500 content | 5.5 mg/ml | 110 mg/ml |
| Mannitol content | 27.5 mg/ml | 27.5 mg/ml |
| Reconstitution time | 19 minutes | 12 minutes |
| Syringibility | Yes | Yes |
| pH | 6.8 | 6.8 |

Additional illustrations of pharmaceutical compositions were produced (see, e.g., Table 2, formulations "1", "2", "3", "4", and "5"), wherein the content of PEG 1500 was selected from an amount ranging between 110 mg/vial (10 weight %) and 330 mg/vial (30 weight %). As shown in Table 2, in producing an injectable solution formulation by reconstituting a lyophilized form of the pharmaceutical composition with 1 ml of water (pharmaceutical grade), the reconstitution time ranged from less than 1 minute to about 5 minutes. Table 2 also shows that the syringibility was acceptable for all formulations of the pharmaceutical composition tested; and the physical stability (e.g., as measured by visual clarity/transparency of the solution at room temperature) was acceptable for all formulations of the pharmaceutical composition tested. Drug product stability studies have also been performed for the pharmaceutical composition according to the present invention in powder form (e.g., lyophilized or precipitated) with the resultant demonstration of stability suitable for pharmaceutical applications known in the art.

TABLE 2

|  | 1 | 2 | 3 | 4 | 5 |
|---|---|---|---|---|---|
| T-1249 (SEQ ID NO:5) content (mg/ml) | 118 | 118 | 118 | 118 | 118 |
| PEG 1500 content (mg/ml) | 110 | 165 | 220 | 275 | 330 |
| Mannitol content (mg/ml) | 27.5 | 27.5 | 27.5 | 27.5 | 27.5 |
| Reconstitution time (minutes) in 1 ml of an aqueous solution | 3–4 | 5 | 3–4 | 3–4 | <1 |
| Syringibility using 27 gauge needle | Yes | Yes | Yes | Yes | Yes |
| Physical stability At room temperature | >4 days | >4 days | >4 days | >4 days | >4 days |

Additional examples of pharmaceutical composition according to the present invention, comprising synthetic peptide in solution with a polyol, were formulated for evaluation for clinical use. Some illustrative examples are provided in Table 3, including pharmaceutical compositions comprising a final concentration of not less than 100 mg/ml of the synthetic peptide ("formulation X", "formulation Y", "formulation Z"), and pharmaceutical compositions comprising a final concentration of 200 mg/ml of the synthetic peptide ("formulation H", "formulation I", "formulation K"). Where there is a pH range indicated in Table 3, sodium hydroxide or acetic acid or other suitable base or acid is used to adjust the pH to a pH in the desired range. Also, formulations H-J contain an alcohol, and more preferably ethanol (200 proof), in a concentration of 120 mg/ml.

TABLE 3

| | X | Y | Z | H | I | J |
|---|---|---|---|---|---|---|
| T-1249 (SEQ ID NO:5) (mg/ml) | 100 | 100 | 100 | 200 | 200 | 200 |
| PEG 1500 (mg/ml) | 92 | 91.7 | 91.7 | 167 | 167 | 167 |
| Mannitol (mg/ml) | 23. | 22.9 | 22.9 | — | — | — |
| pH | 6.5–9.0 | 6.8 | 8.0 | 6.8–9.0 | 6.8 | 8.0 |

Additionally, drug product stability studies have also been performed for the pharmaceutical composition according to the present invention in solution form (e.g., formulation Y of Table 3) by assessing such parameters as content of synthetic peptide, osmolality, pH, and appearance of solution over a 48 hour period and at various temperatures (e.g., 5° C., 25° C., and 40° C.) with no significant changes observed.

EXAMPLE 2

In this example, illustrated is the unexpected result that use of the pharmaceutical composition according to the present invention as an injectable solution may reduce, in both incidence and intensity, injection site reactions when compared to prior known formulations of a pharmaceutical composition comprising synthetic peptide. Using a standard model for injection site reactions known in the art, injection site reactions can be determined experimentally by administering the pharmaceutical composition in the form of an injectable aqueous formulation to be tested by subcutaneous route in rabbits. Typically, the injectable aqueous formulation, as a unit dose, will be used to inject 4 to 5 injection sites per animal. Table 4 shows a comparison of injection site reactions when using an aqueous formulation comprising about 100 mg of synthetic peptide but lacking a polyol ("Formulation C"), versus using an aqueous formulation comprising about 100 mg of synthetic peptide and 10 weight % of a polyol ("Formulation D"; see, e.g., 1 in Table 2), versus using an aqueous formulation comprising about 100 mg of synthetic peptide and 30 weight % of a polyol ("Formulation E"; see, e.g., 5 in Table 2). Each formulation was tested in multiple animals (typically between 7 to 15), and the number of "Affected Sites" is defined as: the number of sites in which an injection reaction was observed/the number of injected sites.

Irritation was scored by visually inspecting the injection site where a respective score was defined as follows:
"0"—no discernable reaction; "1"—slight hyperemia and discoloration; "2"—moderate hyperemia and discoloration; "3"—distinct discoloration in comparison with the surrounding area; "4"—small area of necrosis; and "5"—widespread necrosis, possibly involving underlying muscle.

Irritation was graded by the average of the irritation score as follows: "none"—0.0 to 0.4; "slight"—0.5 to 1.4; "mild"—1.5 to 2.4; "moderate"—2.5 to 3.4; "marked"—3.5 to 4.4.

TABLE 4

| Formulation | # Affected Sites | Avg. Irritation Score | Irritation Grade |
|---|---|---|---|
| C | 11/13 | 3.8 | Marked |
| D | 08/12 | 2.2 | Mild |
| E | 04/12 | 1.2 | Slight |

As shown in Table 4, a pharmaceutical composition comprising a solution comprised of a synthetic peptide (HIV fusion inhibitor in a concentration of no less than 70 mg/ml and no more than 500 mg/ml, and more preferably no less than 100 mg/ml and no more than 250 mg/ml) admixed with a polyol (e.g., in a final concentration of no less than 10 weight % and no more than 50 weight % of the pharmaceutical composition) reduces, in both incidence and intensity, injection site reactions when used as an injectable solution formulation as compared to an injectable formulation comprising an equivalent amount of synthetic peptide but lacking the polyol. Interestingly, when the same formulations (C, D, and E) were made except that synthetic peptide was not included, none of the resultant formulations induced a significant (as measured by Irritation Grade) injection site reaction when administered subcutaneously.

Additionally, use of a polyol as taught in the present invention provides for conditions of solubility and stability in solution to allow amounts greater than 100 mg of synthetic peptide per ml of injectable aqueous formulation of pharmaceutical composition to be achieved. Thus, as compared to formulations (e.g., containing 25 mg/ml or 50 mg/ml) of synthetic peptide known before the present invention, the pharmaceutical composition of the present invention may reduce the number of injections needed to administer an effective amount of synthetic peptide for achieving a therapeutic effect. In this regard, individuals were divided into two groups: individuals dosed with a mannitol formulation (lacking polyol) receiving 2 subcutaneous doses, each dose comprising 48 mg of synthetic peptide (for a total amount of synthetic peptide delivered of 96 mg); and individuals who received a single subcutaneous dose of a pharmaceutical composition according to the present invention (see, e.g., formulation Y of Table 3); each group receiving dosing at the same anatomical site. Prior to analysis for relative bioavailability and bioequivalence (e.g., plasma concentrations, and pharmacokinetic profiles over time), plasma concentrations were adjusted for effective dose. The study results indicate that bioequivalence and bioavailability were comparable between the dosing comprising 2 lower doses of the mannitol formulation with the single dose of the pharmaceutical composition according to the present invention comprising synthetic peptide and a polyol.

In another study, the pharmaceutical composition according to the present invention was compared to the standard mannitol formulation (lacking polyol, as previously described herein) for biological activity (i.e., antiviral potency against HIV-1). In this study, an HIV-1 infection assay was used to determine the respective antiviral potencies of the compared formulations. More particularly, antiviral activity observed using an in vitro infectivity assay ("Magi-CCR5 infectivity assay"; see, e.g., U.S. Pat. No. 6,258,782) has been shown to reasonably correlate to antiviral activity observed in vivo for the same HIV fusion inhibitor peptides (see, e.g., Kilby et al., 1998, Nature Med. 4:1302–1307). These assays score for reduction of infectious virus titer employing the indicator cell lines MAGI or the CCR5 expressing derivative cMAGI. Both cell lines exploit the ability of HIV-1 tat to transactivate the expression of a β-galactosidase reporter gene driven by the HIV-LTR. The β-gal reporter has been modified to localize in the nucleus and can be detected with the X-gal substrate as intense nuclear staining within a few days of infection. The number of stained nuclei can thus be interpreted as equal to the number of infectious virions in the challenge inoculum if there is only one round of infection prior to staining.

Infected cells are enumerated using a CCD-imager and both primary and laboratory adapted isolates show a linear relationship between virus input and the number of infected cells visualized by the imager. In the MAGI and cMAGI assays, a 50% reduction in infectious titer (Vn/Vo=0.5) is significant, and provides the primary cutoff value for assessing antiviral activity ("IC50" is defined as the dilution resulting in a 50% reduction in infectious virus titer). The respective formulations comprising synthetic peptide being tested for antiviral activity were diluted to equivalent concentrations for comparison, and tested in duplicate or triplicate against an HIV inoculum adjusted to yield approximately 1500–2000 infected cells/well of a 48 well microtiter plate. The synthetic peptide (in the respective formulation) was added to the cMAGI or MAGI cells, followed by the virus inocula; and 24 hours later, an inhibitor of infection and cell-cell fusion (e.g., T20, SEQ ID NO:4) was added to prevent secondary rounds of HIV infection and cell-cell virus spread. The cells were cultured for 2 more days, and then fixed and stained with the X-gal substrate to detect HIV-infected cells. The number of infected cells for each control and peptide dilution was determined with the CCD-imager, and then the IC50 was calculated. Comparison of the biological activity of synthetic peptide contained in the mannitol formulation with synthetic peptide contained in a pharmaceutical composition according to the present invention (see, e.g., formulation Y of Table 3), as illustrated in Table 5, shows no significant difference with respect to antiviral potency against HIV-1.

TABLE 5

| Formulation | IC$_{50}$ (ng/ml) |
| --- | --- |
| Mannitol formulation | 3.6 ± 0.2 |
| Pharmaceutical composition (formulation Y) | 3.7 ± 0.4 |

EXAMPLE 3

As apparent to one skilled in the art from the descriptions herein, and due to the similarity in structure, function, and composition of the class of HIV fusion inhibitor peptides (as previously detailed herein), a pharmaceutical composition according to the present invention may be a solution comprised of any one or more of the HIV fusion inhibitor peptides (e.g., at a concentration of no less than 70 mg/ml, and more preferably no less than 100 mg/ml) in admixture with a polyol in a final concentration of no less than 10% by weight and no more than 50% by weight of the pharmaceutical composition, for use as an injectable solution formulation. In that regard, T20 (SEQ ID NO:4) was used as synthetic peptide contained in a pharmaceutical composition according to the present invention. Table 6 shows another illustrative example of the pharmaceutical composition according to the present invention. This example of a pharmaceutical composition, containing a polyol in a final concentration of no less than 10% by weight and no more than 50% by weight of the pharmaceutical composition, also demonstrates a reduction in the reconstitution time, as compared to similar formulation excluding the polyol. Upon visual inspection for over a day, the solution remained stable at room temperature. Antiviral potency (IC$_{50}$ in ng/ml) was determined using the methods outlined in Example 2 herein, and was comparable to that observed for pure drug.

TABLE 6

|  | Reconstituted |
| --- | --- |
| T20 content (SEQ ID NO:4) | 180 mg/ml |
| PEG 1500 content | 208 mg/ml |
| Reconstitution time | <5 minutes |
| Syringibility | Yes |
| pH | Adjusted to 9.0 |
| IC$_{50}$ | 6.6 ± 1.2 |

Further illustrative examples of pharmaceutical compositions are provided in Table 7. As apparent to one skilled in the art, the desired final pH in the range of pHs of from 6.5 to 9.5, may depend on the amount and/or type of polyol, or other factors known in the art, as can be determined using standard methods known in the art.

TABLE 7

| Synthetic peptide | 180 mg | 150 mg | 75 mg |
| --- | --- | --- | --- |
| PEG 1500 content | 208 mg | 125 mg | 125 mg |
| Sodium hydroxide as needed | Adjust to pH 6.5–9.5 | Adjust to pH 6.5–9.5 | adjust to pH 6.5–9.5 |
| Hydrogen chloride or acetic acid as needed | Adjust to pH 6.5–9.5 | Adjust to pH 6.5–9.5 | adjust to pH 6.5–9.5 |
| Sterile water | 1.0 ml | 1.0 ml | 1.0 ml |

EXAMPLE 4

The present invention provides for pharmaceutical compositions which comprises synthetic peptide comprising HIV fusion inhibitors having antiviral activity as evidenced by the ability to inhibit transmission of HIV to a target cell, and/or to inhibit gp41-mediated fusion of HIV to a target cell. Also provided is a method for treating HIV-1 infection comprising administering to an HIV-1-infected individual a pharmaceutical composition according to the present invention. Preferably, the pharmaceutical composition is in an amount effective to inhibit transmission of HIV to a target cell, and/or in an amount effective to inhibit gp41-mediated fusion of HIV to a target cell.

The method may comprise contacting the virus, in the presence of the cell, with a concentration of a pharmaceutical composition according to the present invention effective to inhibit infection of the cell by HIV. Also, the method may comprise adding to the virus and the cell an amount of a pharmaceutical composition according to the present invention effective to inhibit gp41-mediated fusion between the virus and the cell. These methods may be used to treat HIV-infected individuals (therapeutically) or to treat individuals newly exposed to or at high risk of exposure (e.g., through drug usage or high risk sexual behavior) to HIV (prophylactically). Thus, for example, in the case of an HIV-1 infected individual, an effective amount of the pharmaceutical composition would be a dose sufficient (by itself and/or in conjunction with a regimen of doses) to reduce HIV viral load in the individual being treated. As known to those skilled in the art, there are several standard methods for measuring HIV viral load which include, but are not limited to, by quantitative cultures of peripheral blood mononuclear cells and by plasma HIV RNA measurements. In a method according to the present invention, the pharmaceutical composition of the invention can be administered in a single administration, intermittently, periodically, or continuously, as can be determined by a medical practitioner, such as by monitoring viral load. A pharmaceutical composition according to the present invention may show synergistic results, of inhibiting transmission of HIV to a target cell, when used in combination (e.g., when used simultaneously, or in a cycling on with one drug and cycling off with another) with other antiviral drugs used for treatment of HIV (e.g., including, but not limited to, other HIV entry inhibitors (e.g., CCR5 inhibitors, retrocyclin, and the like), HIV integrase inhibitors, reverse transcriptase inhibitors (e.g., nucleoside or nonnucleoside), protease inhibitors, and the like, as well known in the art) (see, e.g., U.S. Pat. No. 6,475,491, the disclosure of which is herein incorporated by reference)

Effective dosages ("concentrations") of a pharmaceutical composition of the invention to be administered may be determined through procedures well known to those in the art; e.g., by determining potency, biological half-life, bioavailability, and toxicity. In a preferred embodiment, an effective dosage range is determined by one skilled in the art using data from routine in vitro and in vivo studies well know to those skilled in the art. For example, in vitro infectivity assays of antiviral activity, such as those known in the art, enables one skilled in the art to determine the mean inhibitory concentration (IC) necessary to block (e.g., inhibit transmission) some amount of viral infectivity (e.g., 50% inhibition, $IC_{50}$; or 90% inhibition, $IC_{90}$). Likewise, in vitro syncytia forming assays may be used to determine a concentration necessary to inhibit gp41-mediated fusion to a target cell. Appropriate doses can then be selected by one skilled in the art using pharmacokinetic data from one or more clinical or experimental studies, so that a minimum plasma concentration (C[min]) of the conjugate is obtained which is equal to or exceeds a predetermined IC value. While dosage ranges typically depend on the route of administration chosen and the formulation of the dosage, an exemplary dosage range of the pharmaceutical composition according to the present invention may range from no less than 0.1 μg/kg body weight and no more than 10 mg/kg body weight; preferably a dosage range of from about 0.1–100 μg/kg body weight; and more preferably, a single unit dosage of between from about 100 mg to about 250 mg of synthetic peptide comprising the pharmaceutical composition according to the present invention.

A pharmaceutical composition of the present invention may be administered to an individual by any means that enables the active agent to reach the target cells (cells that can be infected by HIV). Thus, the pharmaceutical compositions of this invention may be administered by any suitable technique including, but not limited to, parenterally (e.g., intramuscular, intraperitoneal, intravenous, or subcutaneous injection or infusion, intradermal, or implant). The specific route of administration will depend, e.g., on the medical history of the individual, including any perceived or anticipated side effects from such administration, and the formulation of pharmaceutical composition being administered (e.g., the nature of the polyol and synthetic peptide of which the pharmaceutical composition comprises). Most preferably, the administration is by injection (using, e.g., intravenous or subcutaneous means), but could also be by continuous infusion (using, e.g., slow-release devices or minipumps such as osmotic pumps, and the like). A pharmaceutical composition according to the present invention may further comprise one or more pharmaceutically acceptable carriers in addition to the polyol; and may further depend on the solution formulation desired, site of delivery, the method of administration, the scheduling of administration, and other factors known to medical practitioners.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept; and thus, such modifications and/or adaptations are intended to be within the meaning and scope of the appended claims.

---

What is claimed is:

1. A pharmaceutical composition comprised of an aqueous solution comprising synthetic peptide in admixture with a polyol; wherein the synthetic peptide is an HIV fusion inhibitor; wherein the synthetic peptide is in a final concentration in the pharmaceutical composition of not less than 70 mg/ml and not more than 500 mg/ml; and wherein the polyol is in a final concentration of no less than 5 weight % and no more than 75 weight % of the pharmaceutical composition.

2. The pharmaceutical composition according to claim 1, wherein the synthetic peptide is in a final concentration in the pharmaceutical composition of not less than 100 mg/ml and not more than 250 mg/ml.

3. The pharmaceutical composition according to claim 1, wherein the polyol is in a final concentration of no less than 10 weight % and no more than 50 weight % of the pharmaceutical composition.

4. The pharmaceutical composition according to claim 1, wherein the polyol comprises polyethylene glycol.

5. The pharmaceutical composition according to claim 1, further comprising a pharmaceutically acceptable carrier additional to the polyol.

6. A method of treating HIV infection comprising administering to an HIV-infected individual a pharmaceutical composition according to claim 1.

7. A pharmaceutical composition comprised of an aqueous solution comprising synthetic peptide in admixture with a polyol; wherein the synthetic peptide is an HIV fusion inhibitor; wherein the synthetic peptide is in a final concentration in the pharmaceutical composition of not less than 100 mg/ml and not more than 250 mg/mi; and wherein the polyol is in a final concentration of no less than 10 weight % and no more than 50 weight % of the pharmaceutical composition.

8. The pharmaceutical composition according to claim 7, wherein the polyol comprises polyethylene glycol.

9. The pharmaceutical composition according to claim 7, further comprising a pharmaceutically acceptable carrier additional to the polyol.

10. A method of treating HIV infection comprising administering to an HIV-infected individual a pharmaceutical composition according to claim 7.

11. A synthetic peptide-containing pharmaceutical composition as a unit dose, wherein the pharmaceutical composition comprises an aqueous solution comprising: (a) a polyol present as a pharmaceutically acceptable carrier in an amount not less than 5 weight % and not more than 75 weight % of the pharmaceutical composition as a unit dose; and (b) synthetic peptide comprising an HIV fusion inhibitor in a final concentration of the pharmaceutical composition of not less than 70 mg/ml and not more than 500 mg/ml.

12. The synthetic peptide-containing pharmaceutical composition according to claim 11, wherein the synthetic peptide is in a final concentration in the pharmaceutical composition of not less than 100 mg/ml and not more than 250 mg/ml.

13. The synthetic peptide-containing pharmaceutical composition according to claim 11, wherein the polyol is in a final concentration of no less than 10 weight % and no more than 50 weight % of the pharmaceutical composition.

14. The synthetic peptide-containing pharmaceutical composition according to claim 11, wherein the polyol comprises polyethylene glycol.

15. The synthetic peptide-containing pharmaceutical composition according to claim 11, further comprising a pharmaceutically acceptable carrier additional to the polyol.

16. A method of treating HIV infection comprising administering to an HIV-infected individual a synthetic peptide-containing pharmaceutical composition according to claim 11.

17. A synthetic peptide-containing pharmaceutical composition as a unit dose, wherein the pharmaceutical composition comprises an aqueous solution comprising: (a) a polyol present as a pharmaceutically acceptable carrier in an amount not less than 10 weight % and not more than 50% of the pharmaceutical composition as a unit dose; and (b) synthetic peptide comprising an HIV fusion inhibitor in a final concentration of the pharmaceutical composition of not less than 100 mg/ml and not more than 250 mg/ml.

18. The synthetic peptide-containing pharmaceutical composition according to claim 17, wherein the polyol comprises polyethylene glycol.

19. The synthetic peptide-containing pharmaceutical composition according to claim 17, further comprising a pharmaceutically acceptable carrier additional to the polyol.

20. A method of treating HIV infection comprising administering to an HIV-infected individual a synthetic peptide-containing pharmaceutical composition according to claim 17.

21. A method of treating HIV infection comprising administering to an HIV-infected individual a pharmaceutical composition according to claim 5.

22. A method of treating HIV infection comprising administering to an HIV-infected individual a pharmaceutical composition according to claim 9.

23. A method of treating HIV infection comprising administering to an HIV-infected individual a synthetic peptide-containing pharmaceutical composition according to claim 15.

24. A method of treating HIV infection comprising administering to an HIV-infected individual a synthetic peptide-containing pharmaceutical composition according to claim 19.

* * * * *

UNITED STATES PATENT AND TRADEMARK OFFICE
CERTIFICATE OF CORRECTION

| | | |
|---|---|---|
| PATENT NO. | : 7,045,552 B2 | Page 1 of 1 |
| APPLICATION NO. | : 10/663589 | |
| DATED | : May 16, 2006 | |
| INVENTOR(S) | : David Heilman, Jie Di and Brian Bray | |

It is certified that error appears in the above-identified patent and that said Letters Patent is hereby corrected as shown below:

Column 63, line 31, "250 mg/mi" should read --250 mg/ml--.

Column 64, beginning at line 53, insert the following claims.

25. The pharmaceutical composition according to claim 9, wherein the pharmaceutically acceptable carrier, additional to the polyol, comprises an aqueous alcohol.

26. The synthetic peptide-containing pharmaceutical composition according to claim 15, wherein the pharmaceutically acceptable carrier, additional to the polyol, comprises an aqueous alcohol.

27. The synthetic peptide-containing pharmaceutical composition according to claim 19, wherein the pharmaceutically acceptable carrier, additional to the polyol, comprises an aqueous alcohol.

28. A method of treating HIV infection comprising administering to an HIV-infected individual a pharmaceutical composition according to claim 25.

29. A method of treating HIV infection comprising administering to an HIV-infected individual a synthetic peptide-containing pharmaceutical composition according to claim 26.

Signed and Sealed this

First Day of August, 2006

JON W. DUDAS
*Director of the United States Patent and Trademark Office*